(12) United States Patent
Charles

(10) Patent No.: US 9,549,849 B2
(45) Date of Patent: Jan. 24, 2017

(54) SYSTEMS AND METHODS FOR REINJECTION OF PROCESSED VITREOUS HUMOR

(75) Inventor: Steven T. Charles, Memphis, TN (US)

(73) Assignee: Alcon Research, Ltd., Fort Worth, TX (US)

( * ) Notice: Subject to any disclaimer, the term of this patent is extended or adjusted under 35 U.S.C. 154(b) by 1168 days.

(21) Appl. No.: 13/614,483

(22) Filed: Sep. 13, 2012

(65) Prior Publication Data

US 2014/0074011 A1 Mar. 13, 2014

(51) Int. Cl.
*A61K 9/22* (2006.01)
*A61F 9/007* (2006.01)

(52) U.S. Cl.
CPC ....... *A61F 9/00745* (2013.01); *A61F 9/00736* (2013.01)

(58) Field of Classification Search
CPC .......................... A61F 9/00736; A61M 1/0058
USPC ........................................ 604/22, 67, 890.1
See application file for complete search history.

(56) References Cited

U.S. PATENT DOCUMENTS

| | | |
|---|---|---|
| 5,176,628 A | 1/1993 | Charles et al. |
| 5,824,212 A | 10/1998 | Brockhoff |
| 6,290,690 B1 | 9/2001 | Huculak et al. |
| 7,141,048 B1 | 11/2006 | Charles |
| 7,285,107 B1 | 10/2007 | Charles |
| 7,455,657 B2 | 11/2008 | Naimark et al. |
| 7,934,648 B2 | 5/2011 | Charles et al. |
| 7,956,341 B2 | 6/2011 | Gao |
| 8,080,029 B2 | 12/2011 | Charles |
| 8,251,980 B2 | 8/2012 | Zica et al. |
| 8,905,930 B2 | 12/2014 | Charles |
| 2004/0092861 A1* | 5/2004 | Quiroz-Mercado A61M 1/0058 604/22 |
| 2006/0058729 A1 | 3/2006 | Urich |
| 2010/0260815 A1* | 10/2010 | Kyle ...................... A61K 35/14 424/422 |
| 2011/0112472 A1* | 5/2011 | Jacobson ............ A61F 9/00736 604/67 |

FOREIGN PATENT DOCUMENTS

| | | |
|---|---|---|
| EP | 2397114 A1 | 12/2011 |
| WO | 2014/042832 A1 | 3/2014 |

OTHER PUBLICATIONS

International Searching Authority, International Search Report, PCT/US2013/055737, Mar. 20, 2014, 2 pages.

(Continued)

*Primary Examiner* — Phillip Gray

(57) ABSTRACT

A system for the removal of vitreous humor and other fluids from an eye and the reinjection of filtered vitreous humor into the eye is provided. The system comprises a hollow removal device, a filter, and an infusion device. The removal device includes an element configured to cut the vitreous humor and is configured to aspirate the vitreous humor from the eye. The filter is configured to create a filtered form of vitreous humor by separating the vitreous humor from undesired components in the vitreous humor. The infusion device is fluidly coupled to the filter and is configured to return the filtered form of vitreous humor into the eye.

7 Claims, 6 Drawing Sheets

(56) References Cited

OTHER PUBLICATIONS

International Searching Authority, Written Opinion of the International Searching Authority, PCT/US2013/055737, Nov. 13, 2013, 5 pages.

Blana, SA. et al. "Variations in vitreous humor chemical values as a result of pre-analytical treatment". Forensic Science International, Jul. 15, 2011, vol. 210, 263-270, 8 pgs.

Brunish, R. et al. "Proteins and Hyaluronic Acid of Beef Vitreous Humor". Trans Am Ophthamol. Soc., 1954, vol. 52, 369-387, 19 pgs.

* cited by examiner

SYSTEMS AND METHODS FOR REINJECTION OF PROCESSED VITREOUS HUMOR

BACKGROUND

The vitreous body is a clear, transparent gelatinous substance in the vitreous cavity of the eye that is posterior to the lens and anterior to the retina. The vitreous body occupies two thirds of the ocular volume, having a weight of approximately 4 g and a volume of about 4 mL. The main components of the vitreous body include water (98%), collagen fibrils, glycosaminoglycans, and hyaluronic acid (HA). It functions to give shape to the eye, transmit light, and form a semi-solid support scaffold for the retina. Specific diseases, age-related degeneration, and/or trauma can lead to pathological changes in the vitreous body, including HA degeneration and collagen precipitation, which may result in liquefaction of the vitreous matrix. A degenerated or liquefied vitreous body can lead to floater formation (e.g., cellular debris and deposits of various size, shape, consistency, refractive index, and motility within the eye's normally transparent vitreous humor which can obstruct vision), posterior vitreous detachment, epimacular membrane macular schisis, macular hole, vitreomacular traction, and possible retinal breaks and detachment, all of which may result in a loss of vision.

Vitrectomy is surgery to remove some or all of the vitreous humor from the eye. The original purpose of vitrectomy was to remove clouded vitreous from the eye. Among clinical treatments today, pars plana vitrectomy (PPV) is a common surgery for treating a number of ocular diseases, including diabetic retinopathy, retinal detachment, vitreous hemorrhage, and macular holes. During PPV, the vitreous body is cut and aspirated out of the eye, and then (after additional surgical steps if needed) may be replaced with a vitreous substitute such as gas (air, perfluoropropane, or sulfur hexafluoride) or silicone oil. Vitreous substitutes are used to fill the vitreous cavity and help reattach the retina after surgery. Postoperatively, a vitreous substitute can keep the retina in position while the adhesion between the retina and the retinal pigment epithelium cells forms.

Considerations for vitreous substitutes include clarity, transparency, refractive index similar to natural vitreous humor, ability to allow metabolite transfer, non-absorbable characteristics, hydrophilic composition, and the ability to be injected through a small-gauge needle. Moreover, the substitute should be generally non-toxic, non-inflammatory, and non-immunogenic without being easily degraded or decomposed. Thus, it has been challenging to provide a suitable vitreous substitute.

Dispersive ophthalmic viscoelastics (OVDs) are frequently used to maintain the clarity and integrity of the globe during vitrectomy procedure. However, studies have shown that OVDs may cause or aggravate glaucoma if left in the eye too long and OVDs diffuse out of the eye. Infusion fluids such as balanced salt solution (BSS or BSS Plus) cannot supply long-lasting vitreous substitutes because they are replaced within hours. Gases injected into the posterior segment of the globe are useful for flattening a detached retina against the globe and keeping it attached as healing occurs. However, gases can raise the intraocular pressure, causing possible occlusion of the central retinal artery. Contact of the gas with the lens can induce cataract formation, and contact of the gas with the corneal endothelium can cause corneal damage. Gases are also rapidly reabsorbed from the vitreous cavity within a few days. Rapid elimination prevents the gases from supporting the retina long enough to promote effective healing. In addition, it is often necessary for the patient to maintain an uncomfortable prone position for a week or more following surgery when gas is used to prevent pupillary block glaucoma. Silicone oil has been used instead of gases for complicated retinal detachments or in patients (e.g., children) who are unable to maintain such positioning post-operatively, but silicone oil self-emulsifies (requiring removal and possible retinal detachment) and long-term complications from the silicone oil can include cytotoxicity to ocular tissue, cataract, and emulsification glaucoma. In addition, most of the current vitreous substitutes lack hyalocytes, hyaluronan, ascorbic acid, and other factors that are present in vitreous humor. Some of these factors, particularly ascorbate, may function to prevent nuclear sclerotic cataract formation, which is partly due to oxidation reactions, via their anti-oxidant properties.

Accordingly, there exists a need for an improved vitreous substitute. The systems and methods disclosed herein overcome one or more of the deficiencies of the prior art.

SUMMARY

In one exemplary embodiment, the present disclosure describes a system for processing vitreous humor and other fluids removed from an eye. The system comprises a filter for removing undesirable components from the vitreous humor. In still a further form, the system includes a concentrator. In one aspect, the concentrator is configured to receive the vitreous humor and to create a concentrated form of vitreous humor by separating the vitreous humor from the other fluids. In one aspect, the filter is fluidly coupled to the concentrator and is configured to create a filtered form of vitreous humor by separating the vitreous humor from undesired components in the vitreous humor.

In another exemplary embodiment, the present disclosure describes a system for the removal of vitreous humor and other fluids from an eye and the reinjection of filtered vitreous humor into the eye. In one aspect, the system comprises a hollow removal device and a filter. The hollow removal device includes a vitreous humor shearing element, and is configured to aspirate the vitreous humor from the eye. The filter is configured to create a filtered form of vitreous humor by separating the vitreous humor from undesired components in the vitreous humor. In one aspect, the system comprises a hollow removal device, a filter, and an infusion device fluidly coupled to the filter and configured to return the filtered form of vitreous humor into the eye.

In another exemplary embodiment, the present disclosure describes a method of removing vitreous humor and other fluids from an eye and injecting processed vitreous humor into the eye. In one aspect, the method comprises inserting a hollow removal device configured to aspirate the vitreous humor from the eye into a posterior segment of the eye, the removal device including an element configured to cut the vitreous humor; inserting a fluid infusion device into the eye; cutting the vitreous humor with the hollow removal device; aspirating the vitreous humor and other fluids from the eye into a processing system using the hollow removal device while infusing fluid into the eye through the fluid infusion device; creating processed vitreous substitute within the processing system by removing undesired components out of the vitreous humor; and infusing the processed vitreous substitute into the eye through the fluid infusion device.

In some embodiments, creating a processed vitreous substitute within the processing system by removing undesired components out of the vitreous humor comprises concentrating the vitreous humor by separating the vitreous humor from irrigation fluids.

In some embodiments, creating a processed vitreous substitute within the processing system by removing undesired components out of the vitreous humor filtering undesired components out of the vitreous humor.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
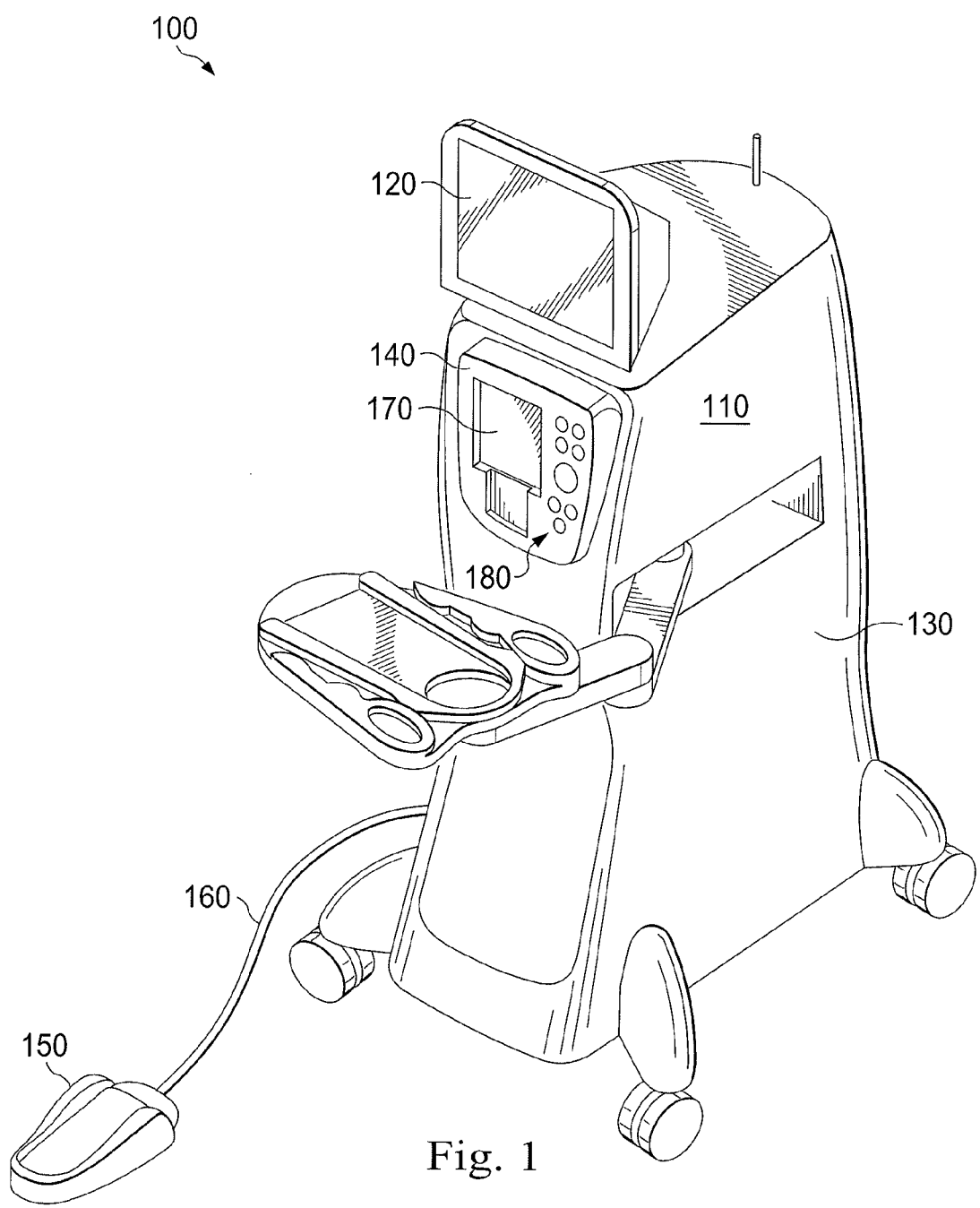
FIG. 1 illustrates a perspective view of a microsurgical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to vitreous replacements, and more specifically to vitreous humor substitutes and the systems and methods involved in making and using the vitreous humor substitutes. In some instances, embodiments of the present disclosure are configured to be part of an ophthalmic surgical system. Instead of supplying a synthetic or non-autologous vitreous substitute, the vitreous substitutes disclosed herein comprise a processed (i.e., cut and filtered) form of the patient's own vitreous humor. Using a conventional vitrectomy surgical system and a processing system, the vitreous humor is removed from the patient's eye, processed, and re-injected into the patient's eye during the vitrectomy procedure. In some embodiments, the processing system includes a concentrator and a filter that are configured to separate the cellular debris, certain cells, blood, and infusion fluid from the aspirated vitreous humor to produce a processed form of the vitreous. The processed vitreous lacks the cellular debris previously present in the patient's vitreous, but may retain the hyalocytes, hyaluronan, ascorbic acid, and other factors (including antioxidants) that are normally present in vitreous humor. Thus, unlike several other vitreous substitutes, the processed vitreous disclosed herein may retain cells and factors that are helpful in preventing nuclear sclerotic cataract. Additionally, the processed vitreous may be left permanently in the patient's eye without generating an immunological, inflammatory, or toxic response. Therefore, the systems and methods disclosed herein utilizes conventional vitrectomy surgical tools and a processing system to re-inject processed vitreous that retains several helpful substances into the patient's eye, thereby allowing for autologous transplantation of a processed form of a patient's own vitreous humor during a conventional vitrectomy procedure.

FIG. 1 illustrates a microsurgical system 100 according to one embodiment of the present disclosure. Though the microsurgical system 100 shown in FIG. 1 is an ophthalmic microsurgical system, the microsurgical system may be any microsurgical system. The system 100 is capable of providing pneumatic drive pressure or electrically actuated cutter drive currents and voltages and aspiration vacuum to a vitrectomy probe and irrigation fluid to an irrigation cannula in an ophthalmic surgical procedure. The system 100 may be capable of providing electrical power, ultrasound power, irrigation fluid, and aspiration vacuum to an ultrasonic handpiece as well in an ophthalmic surgical procedure.

In the pictured embodiment, the system 100 includes a cartbody 110, a graphic user interface 120 attached to the cart body 110, a footswitch interface controller (FIC) 130 disposed within the cart body 110, a control console 140 disposed on a surface of the body 110, and a proportional controller or footswitch 150 connected to the FIC 130 via a bi-directional bus or cable 160. In some embodiments, the footswitch is replaced by another suitable form of proportional controller, such as, by way of non-limiting example, a handswitch. The control console 140 includes a cassette receiving area 170 and a plurality of ports 180. A surgical cassette can be operatively coupled to the system 100 via the cassette receiving area 170 to manage the fluidics of the system 100. The bi-directional bus 160 sends signals in either direction between the FIC 130 and the footswitch 150, and may be used to transmit power to the footswitch 150. In some embodiments, the FIC 130 and the footswitch 150 communicate through a wireless connection.

During ophthalmic surgery, a series of handpieces may be coupled to the system 100, typically via conventional flexible plastic, silicone, or rubber tubing fluidly coupled with the surgical cassette and/or electric cabling to operatively connect to the system 100 through one or more of the ports 180. One exemplary handpiece is a vitrectomy probe. Other exemplary handpieces that are utilized in posterior segment ophthalmic surgery include, by way of non-limiting example, an extrusion handpiece, an infusion cannula, microsurgical scissors, and a diathermy handpiece. Some exemplary handpieces that are utilized in anterior segment ophthalmic surgery include, for example, an irrigation handpiece, an irrigation/aspiration handpiece, an ultrasonic (phacoemulsification) handpiece, and a diathermy handpiece.

The system 100 may include a control module, processor, random access memory (RAM), read only memory (ROM), input/output circuitry such as the bus 160, an audio output device, and other components of microsurgical systems well known to those in the art. A control module and/or processor may allow for efficient direction of and communication with other system components, such as the control console 140 and/or the FIC 130. The processor may include one microprocessor chip, multiple processors and/or co-processor chips, and/or digital signal processor capability. In other embodiments, the body may lack a control module and/or processor and therefore, processing and control may be entirely performed on the FIC 130 of the microsurgical system 100. In wireless embodiments, communication between control module and/or processor and other components of the microsurgical system 100 may occur through a series of transmitting and receiving components onboard the footswitch 150 and within the body 110. The control module, the processor, and/or the FIC may be capable of implementing feedback control.

A variety of peripheral devices may also be coupled to the system 100, such as storage devices (hard disk drive, CD ROM drive, etc.), printers, and other input/output devices.

Figure 2:
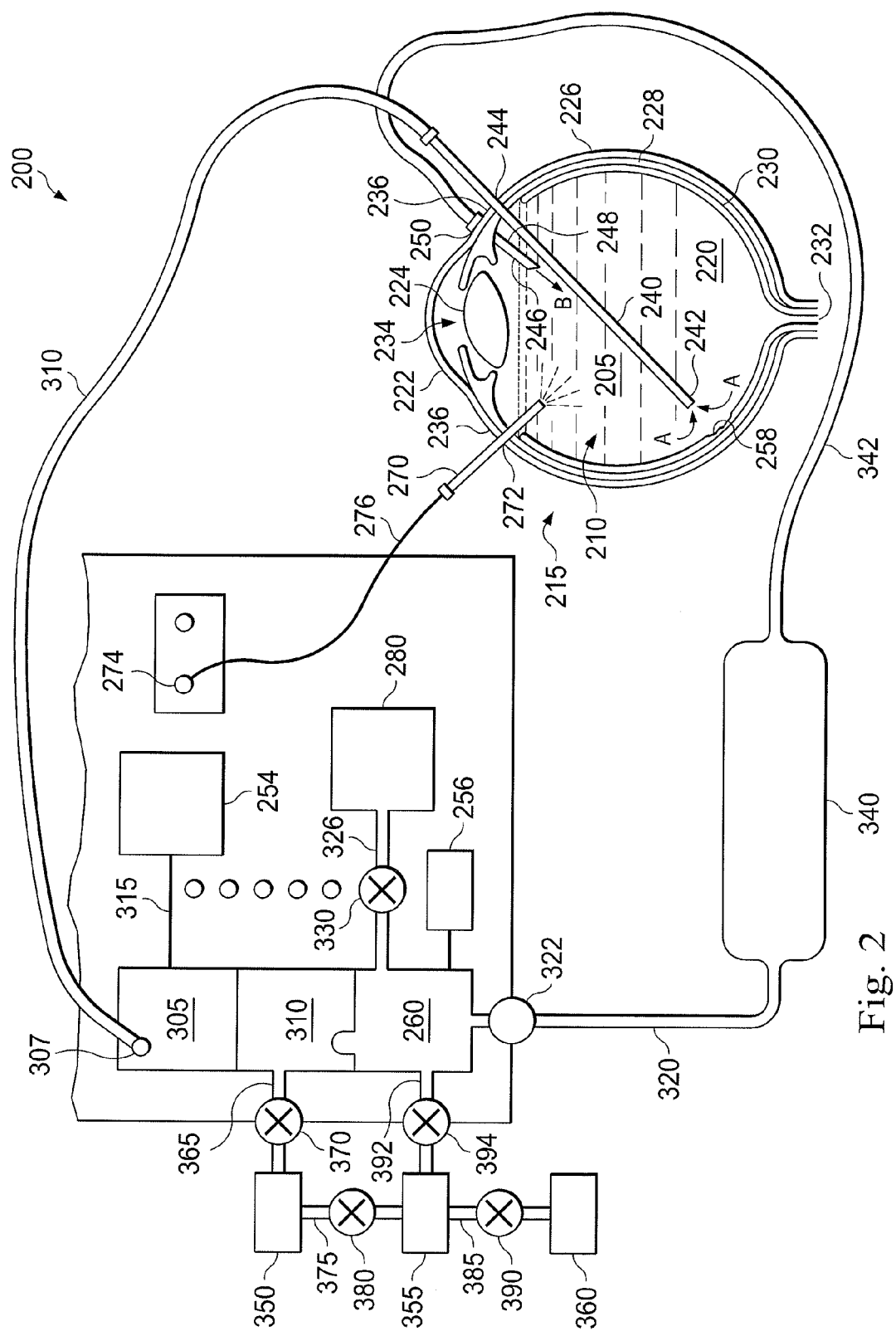
FIG. 2 is a schematic, fragmentary, partially sectional illustration of a microsurgical system for injecting a material into an eye while simultaneously aspirating a second material from the eye according to one embodiment of the present disclosure.

FIG. 2 shows a schematic illustration of a surgical system 200 injecting a first fluid 205 into a posterior segment 210 of a human eye 215 while aspirating a second fluid 220 out of the eye 215 according to an exemplary method of the present disclosure. The surgical system 200 comprises a conventional surgical system capable of performing vitreoretinal surgery that has been modified according to the present disclosure. An exemplary surgical system suitable for such modification is the Accurus® surgical system sold by Alcon Laboratories, Inc. For example, in some embodiments, the surgical system 200 may comprise the microsurgical system 100 shown in FIG. 1. The surgical system 200 is described in further detail below with reference to FIG. 3.

The eye 215 includes a cornea 222, a lens 224, a sclera 226, a choroid 228, a retina 230, and an optic nerve 232. The cornea 222 and the lens 224 generally define an anterior segment 234 of the eye 215. The lens 224, the choroid 228, and the retina 230 generally define the posterior segment 210 of the eye 215. The retina 230 is physically attached to retinal pigment epithelium and the choroid 228 in a circumferential manner proximate the pars plana 236.

As shown in FIG. 2, the eye 215 is undergoing a vitrectomy procedure, during which the second fluid 220 is cut and aspirated out of the posterior segment 210 of the eye 215 by a removal device 240 while the first fluid 205 is being infused into the eye 215. In the pictured embodiment, the second fluid 220 comprises vitreous humor. In some embodiments, during the vitrectomy procedure, the first fluid 205 comprises either an infusion fluid or a processed vitreous substitute. The infusion fluid may be any suitable infusion fluid, such as, by way of non-limiting example, balanced salt solution (BSS) or BSS Plus® intraocular irrigating solution available from Alcon Laboratories, Inc. In some embodiments, the first fluid is less viscous than the second fluid.

A distal tip or hollow needle 242 of the removal device 240 is inserted through a first incision 244 in the pars plana 236 of the eye 215. The removal device 240 may comprise an aspiration device for removing and transporting fluid from the eye 215, and more specifically, may comprise a vitrectomy probe including a hollow needle, with a blade or other cutting device (not shown) mounted for reciprocation within the needle. The cutting device includes any suitable device that can cut, shear, morselize, shred, rip, trim, clip, crop, or otherwise separate the collagen fibers into shorter or smaller segments. A suitable probe, as well as its control module, is included in the commercially available Accurus® surgical system sold by Alcon Laboratories, Inc. A distal tip 246 of a fluid infusion device 248 is inserted through a second incision 250 in the pars plana 236. In some embodiments, the fluid infusion device 248 comprises an infusion cannula. In some embodiments, the fluid infusion device 248 is inserted transconjunctivally at a location 90-180° from the first incision 244.

The cutting device within the removal device 240 is actuated to cut the collagen fibers in the second fluid 220 (i.e., the vitreous humor) into shorter segments, and a vacuum generator 254 is actuated to begin drawing the second fluid 220 in the direction of the arrows A through the removal device 240. At substantially the same time, a pump 256 is actuated to deliver the first fluid 205 from an infusion chamber 260 to the posterior segment 210 of the eye 215 in the direction of arrow B through the fluid infusion device 248. The vacuum generator 254 may be any suitable device for generating vacuum but is preferably a vacuum chip or a venturi chip. The pump 256 may be any suitable device for generating vacuum, including, by way of non-limiting example, a peristaltic pump, a scroll pump, or a vane pump. In some embodiments, the vacuum generator and the pump may comprise a single device.

The flow rate of the first fluid 205 entering the posterior segment 210 is controlled by the surgical system 200 such that it substantially equals the flow rate of the second fluid 220 exiting the posterior segment 210, resulting in a substantially constant volume of fluid in the eye 215 and the maintenance of an appropriate intraocular pressure. In some embodiments, the surgeon may choose the desired vacuum or pressure level by manipulating the proportional controller or footswitch 150 to generate a control signal that is interpreted by the surgical system 200 to affect the flow rate.

In some embodiments, a detached portion or tear 258 of the retina 230 is repositioned as the injection of the first fluid 205 into the posterior segment 210 causes the detached portion or tear 258 to flatten against the choroid 228. In some embodiments, a diathermy probe, laser, and/or adhesive (not shown) is subsequently used to fuse the repositioned portion or tear 258 in place. During the vitrectomy procedure (and/or any subsequent procedures), a conventional fiber optic light source 270 is used to provide light for the surgeon, who may view the posterior segment 210 through a microscope (not shown). In FIG. 2, the light source 270 is shown inserted into the posterior segment 210 through a sclerotomy or third incision 272. In the pictured embodiment, the light source 270 is operatively coupled to a port 274 of the surgical system 200 via a light fiber cable 276.

Figure 3:
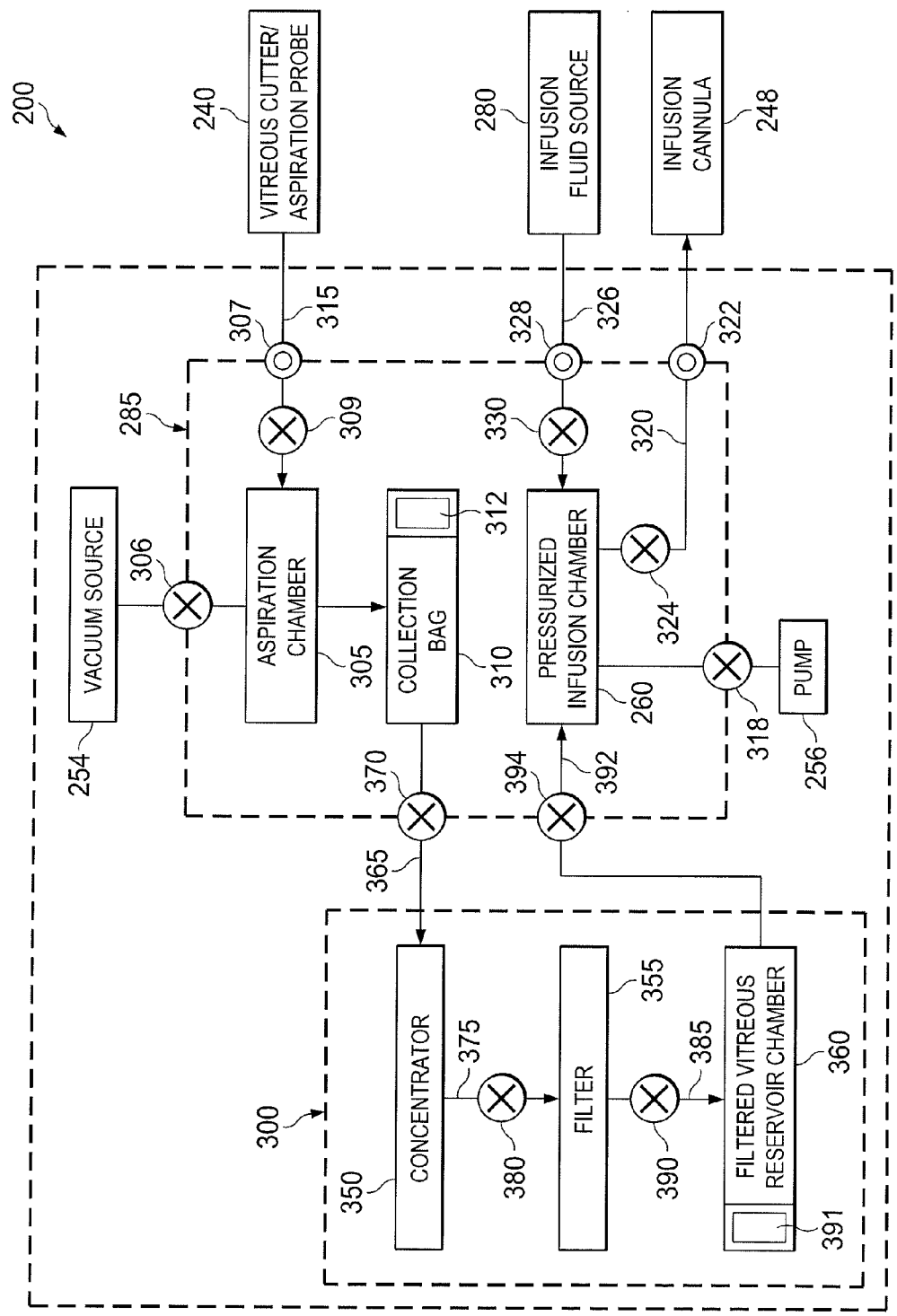
FIG. 3 is a schematic box diagram illustrating component parts of the microsurgical system depicted in FIG. 2 according to one embodiment of the present disclosure.

FIG. 3 is a schematic box diagram illustrating various components of the surgical system 200 according to one exemplary embodiment of the present disclosure. The surgical system 200 comprises a liquid vitrectomy cassette 285, which is coupled to the vacuum source 254, the pump 256, the removal device 240 (e.g., the vitreous cutter and aspiration probe), the fluid infusion device 248, a fluid infusion source 280, and a processing system 300.

The liquid vitrectomy cassette 285 may comprise a conventional surgical cassette that is used in vitrectomy procedures and is configured to hold fluids for aspiration and infusion. In the pictured embodiment, the liquid vitrectomy cassette 285 includes an aspiration chamber 305 connected to a collection bag 310, and the infusion chamber 260.

The aspiration chamber 305 is configured to contain the second fluid 220 and is fluidly coupled to the vacuum source 254, which provides adequate vacuum to withdraw the second fluid 220 from the eye 215. A vacuum control valve 306 is disposed between the vacuum source 254 and the aspiration chamber 305, and is configured to control the delivery of vacuum to the aspiration chamber 305. An aspiration conduit 315 fluidly couples the aspiration chamber 305 to the removal device 240. An aspiration port 307 is between the removal device 240 and the aspiration chamber 305, and an aspiration valve 309 is between the aspiration port and the aspiration chamber 305. The aspiration valve 309 is configured to transition between an open condition and a closed condition. In some embodiments, the open/closed condition of the aspiration valve 309 is responsive to control signals from the surgical system 200 (e.g., from a control module, which may be operably coupled to the pump 256 and/or the vacuum source 254 as shown in FIG. 5).

When the aspiration valve 309 is in an open condition and the vacuum source 254 is actuated, the second fluid 220 is withdrawn from the eye 215 through the removal device 240. As shown in FIG. 2, the second fluid 220 travels through the removal device 240 into the aspiration conduit 315 before flowing past the aspiration port 307 and entering the aspiration chamber 305. The aspiration conduit 315 may be any type of suitable tubing, including, by way of non-limiting example, conventional PVC, silicone, or rubber tubing.

The collection bag 310 is fluidly coupled to the aspiration chamber 305 and the processing system 300. The collection bag 310 is configured to receive the second fluid 220 from the aspiration chamber 305. In some embodiments, the collection bag 310 is fluidly coupled to the cassette 285, and is not a part of the cassette itself. In some embodiments, the collection bag is a container rather than a bag. Some embodiments lack a collection bag, and the aspiration chamber 305 is fluidly coupled to the processing system 300.

In the pictured embodiment, the collection bag 310 is coupled to a fluid level sensor 312, which is configured to measure the level of fluid within the collection bag. The fluid level sensor 312 may be any suitable device for measuring the level of a fluid within a container (e.g., a bag or chamber). Preferably, the fluid level sensor is capable of measuring fluid levels in a continuous manner. In some embodiments, the fluid level sensor can measure the fluid level in a non-invasive manner, such as, by way of non-limiting example, through the use of optics. For example, in some embodiments, the fluid level sensor comprises a linear sensor array as described in U.S. Pat. No. 7,956,341 to Gao, which is herein incorporated by reference in its entirety. In embodiments lacking a collection bag, the aspiration chamber 305 is coupled to the fluid level sensor 312.

The infusion chamber 260 is configured to receive and contain either the first fluid 205 or the second fluid 220. The infusion chamber 260 will be described in further detail below with reference to the second fluid 220 and the processing system 300.

Regarding the first fluid 205, the infusion chamber is fluidly coupled to the pump 256, which provides adequate pressure and/or vacuum to propel the first fluid 205 into the eye 215. In some embodiments, the infusion chamber 260 is pressurized. A pump control valve 318 is disposed between the pump 256 and the infusion chamber 260, and is configured to control the delivery of pressure and/or vacuum to the infusion chamber 260. The fluid infusion device 248 is fluidly coupled to an infusion conduit 320 via an infusion port 322. The infusion port 322 is between the fluid infusion device 248 and the infusion chamber 260, and an infusion valve 324 is between the infusion port and the infusion chamber 260. The infusion chamber 260 is fluidly coupled to the infusion fluid source 280 by a fluid source conduit 326 having a fluid source port 328 and a fluid source valve 330. The infusion fluid source 280 may contain any suitable infusion fluid, such as, by way of non-limiting example, balanced salt solution (BSS) or BSS Plus® intraocular irrigating solution. Both the infusion valve 324 and the fluid source valve 330 are configured to transition between an open condition and a closed condition. In some embodiments, the open/closed conditions of the valves 324, 330 are responsive to control signals from the surgical system 200 (e.g., from a control module, which may be operably coupled to the pump 256 and/or the vacuum source 254 as shown in FIG. 5).

When the infusion valve 324 is in an open condition and the pump 256 is actuated, the first fluid 220 is propelled into the eye 215 through the fluid infusion device 248. In the embodiment shown in FIG. 2, the first fluid 205 flows from the infusion chamber 260, through the infusion port 322, through the infusion conduit 320, through an injection apparatus 340, and through a conduit 342 before entering the eye 215 through the fluid infusion device 248. The conduits 320, 342 may be any type of suitable tubing, including, by way of non-limiting example, conventional PVC, silicone, or rubber tubing. In some embodiments, the injection apparatus 340 comprises a conventional syringe having a plunger movably disposed within a hollow body.

In the pictured embodiment shown in FIGS. 2 and 3, the processing system 300 comprises a concentrator 350, a filter 355, and a filtered vitreous reservoir chamber 360. In some embodiments, the concentrator and the filter may be combined into one device. The concentrator 350 is fluidly coupled to the collection bag 310 and the filter 355. The concentrator 350 is configured to receive the second fluid 220 from the collection bag 310 via a concentration conduit 365. In the pictured embodiment, the processing system 300 includes a concentration valve 370 disposed between the collection bag 310 and the concentrator 350. The concentration valve 370 is configured to transition between an open condition allowing flow into the concentrator 350 and a closed condition preventing flow into the concentrator 350. In some embodiments, the open/closed condition of the valve 370 is responsive to control signals from the surgical system 200 (e.g., from a control module as shown in FIG. 5). The concentrator 350 is configured to concentrate the second fluid 220 by separating the infusion fluid (from the infusion fluid source 280) from the vitreous humor, both of which were likely aspirated from the eye. The concentrator 350 may accomplish this separation by any of a variety of means, including, without limitation, centrifugal separation (e.g., rotary centrifuge, hydrocyclone, or Yaz-Dehydrone), gravity separation, extraction, evaporation, flocculation, or distillation. The irrigation fluid may be collected in a separate container (not shown) and discarded.

The filter 355 is fluidly coupled to the concentrator 350 and the filtered vitreous reservoir chamber 360. The filter 355 is configured to receive the concentrated form of the second fluid 220 from the concentrator 350 via a filtration conduit 375. In the pictured embodiment, the processing system 300 includes a filtration valve 380 disposed between the concentrator 350 and the filter 355. The filtration valve 380 is configured to transition between an open condition allowing flow into the filter 355 and a closed condition preventing flow into the filter 355. In some embodiments, the open/closed condition of the filtration valve 380 is responsive to control signals from the surgical system 200 (e.g., from a control module as shown in FIG. 5). The filter 355 is configured to isolate the vitreous humor from the undesired components in the concentrated form of the second fluid 220 by separating the undesired or non-native components from the vitreous humor. Such undesired components include, by way of non-limiting example, red blood cells, white blood cells, cellular debris, foreign bodies, infectious material, and non-native particulates and precipitates (e.g., calcium). The filter 355 may accomplish this separation by any of a variety of means, including, without limitation, mesh separation techniques, microfiltration, ultrafiltration, nanofiltration, membrane separation techniques (e.g., utilizing a disposable microfiber filter), and/or centrifugal separation techniques (e.g., utilizing rotary centrifuge, hydrocyclone, or Yaz-Dehydrone). The undesired components may be collected in a separate container (not shown) and discarded.

In some embodiments, the filter 355 is configured to receive the second fluid 220 from the collection bag 310, and the second fluid 220 is filtered within the filter before passing into the concentrator 350. In some embodiments, as mentioned above, the filter 355 and the concentrator 350 are a single device. For example, in at least one embodiment, the second fluid 220 is concentrated and filtered in a single filter cartridge, which comprises a membrane or series of membranes configured to separate the vitreous humor from undesired components, including irrigation solution such as BSS, resulting in processed vitreous humor suitable for reinjection into the patient's eye.

In some embodiments, certain filtered elements may be reinfused into the concentrated and filtered form of the second fluid 220. These filtered elements may include hyaluronan, ascorbate, and/or short collagen fragments. In some embodiments, this re-infusion is performed after the second fluid 220 has passed into the filtered vitreous reservoir chamber 360.

The filtered vitreous reservoir chamber 360 is fluidly coupled to the filter 355 and the infusion chamber 260. The filtered vitreous reservoir chamber 360 is configured to receive the concentrated and filtered form of the second fluid 220 from the filter 355 via a reservoir conduit 385. The filtered vitreous reservoir chamber 360 is configured to collect the concentrated and filtered form of the second fluid 220 after it is filtered by the filter 355. In the pictured embodiment, the processing system 300 includes a reservoir valve 390 disposed between the filter 355 and the filtered vitreous reservoir chamber 360. The reservoir valve 390 is configured to transition between an open condition allowing flow into the filtered vitreous reservoir chamber 360 and a closed condition preventing flow into the filtered vitreous reservoir chamber 360. In some embodiments, the open/closed condition of the reservoir valve 390 is responsive to control signals from the surgical system 200 (e.g., from a control module as shown in FIG. 5). Some embodiments lack a reservoir valve, and the vitreous humor components of the second fluid 220 may drain directly from the filter 355 into the filtered vitreous reservoir chamber 360 after being filtered.

In the pictured embodiment, the filtered vitreous reservoir chamber 360 is coupled to a fluid level sensor 391, which is configured to measure the level of fluid within the collection bag. The fluid level sensor may be substantially similar to the fluid level sensor 312, or may comprise a different type of fluid level sensor. The fluid level sensor 391 may be any suitable device for measuring the level of a fluid within a container (e.g., a bag or chamber). Preferably, the fluid level sensor is capable of measuring fluid levels in a continuous manner. In some embodiments, the fluid level sensor can measure the fluid level in a non-invasive manner, such as, by way of non-limiting example, through the use of optics. For example, in some embodiments, the fluid level sensor comprises a linear sensor array as described in U.S. Pat. No. 7,956,341 to Gao, which was incorporated by reference in its entirety above.

The infusion chamber 260 is configured to receive the concentrated and filtered form of the second fluid 220 from the filtered vitreous reservoir chamber 360. The infusion chamber is fluidly coupled to the filtered vitreous reservoir chamber 360 via a vitreous infusion conduit 392. A vitreous infusion control valve 394 is disposed between the filtered vitreous reservoir chamber 360 and the infusion chamber 260, and is configured to control the delivery of the concentrated and filtered form of the second fluid 220 to the infusion chamber 260. In some embodiments, the open/closed condition of the vitreous infusion control valve 394 is responsive to control signals from the surgical system 200 (e.g., from a control module as shown in FIG. 5). At this point, the concentrated and filtered form of the second fluid 220 (e.g., the vitreous substitute or processed vitreous humor) is known as the first fluid 205, and is transferred from the infusion chamber 260 to the eye 215 by travelling through the infusion port 322, the infusion conduit 320, the injection apparatus 340, the conduit 342, and the fluid infusion device 248.

The conduits 365, 375, 385, 392 may be any type of suitable tubing, including, by way of non-limiting example, conventional PVC, silicone, or rubber tubing.

Figure 4:
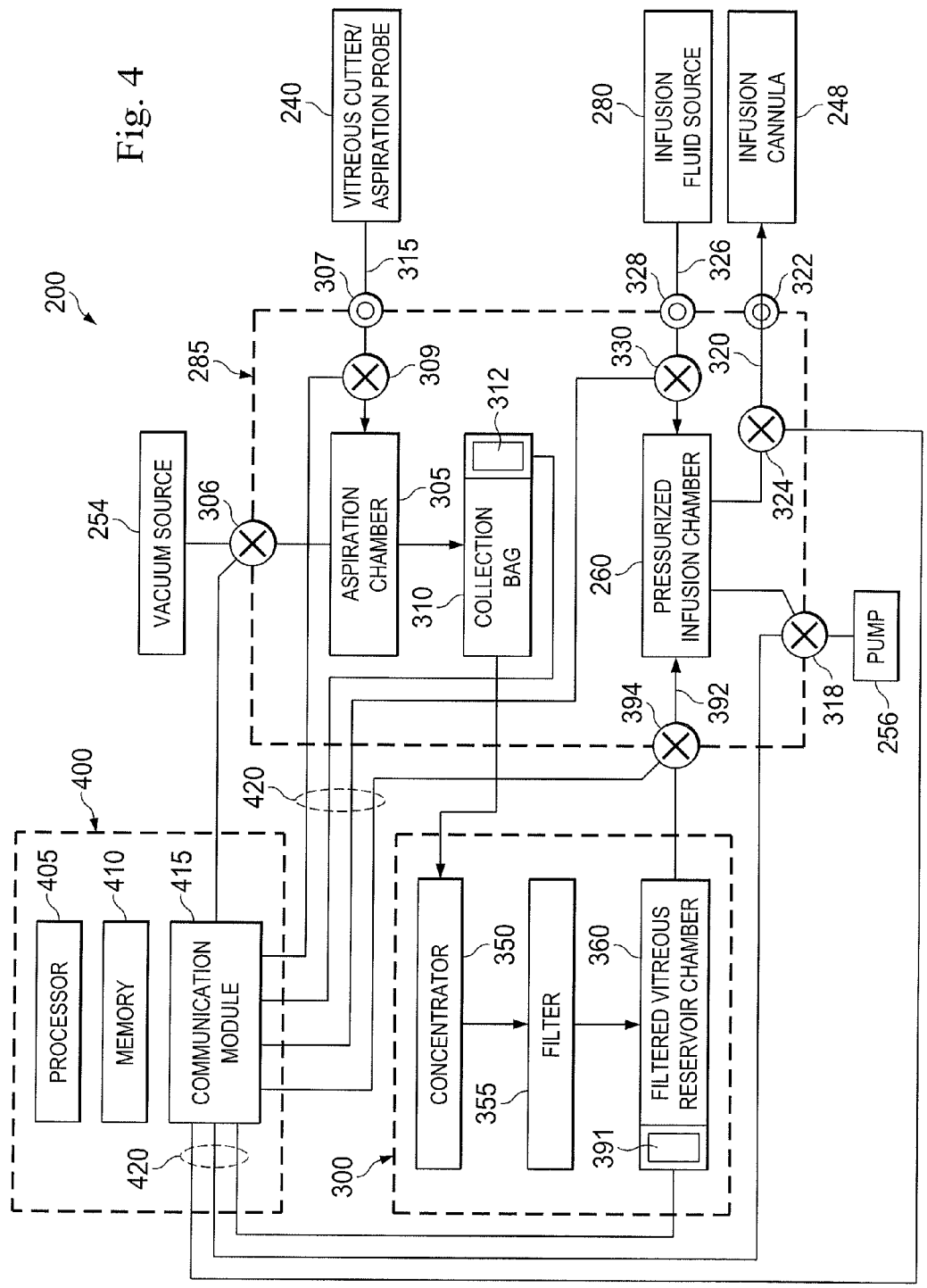
FIG. 4 is a schematic box diagram illustrating component parts of the microsurgical system depicted in FIG. 2 according to one embodiment of the present disclosure.

In the embodiment shown in FIG. 4, the surgical system 200 includes a control module 400, which comprises a processor 405, a memory 410, and a communication module 415. The communication module 415 is electronically coupled to the valves 306, 309, 318, 324, 330, 370, 380, 390, and 394 via control lines 420. In the pictured embodiment, the communication module 415 is also electronically coupled to the fluid level sensors 312, 391. The control module 400 is able to receive signals from the fluid level sensors 312, 391. The control module 400 controls the opening and closing of the valves 306, 309, 318, 324, 330, 370, 380, 390, and 394 based upon information received by the communications module 415, information stored in the memory 410, and/or information interpreted and/or calculated by the processor 405. The control module 400 is capable of implementing feedback control, including, in some instances, proportional-integral-derivative (PID) control. The control module 400 is operably coupled to the pump 256 and the vacuum source 254, and is able to control the actuation of the pump 256 and the vacuum source 254 to affect the fluidics of the system 200 as described above.

Figure 5A:
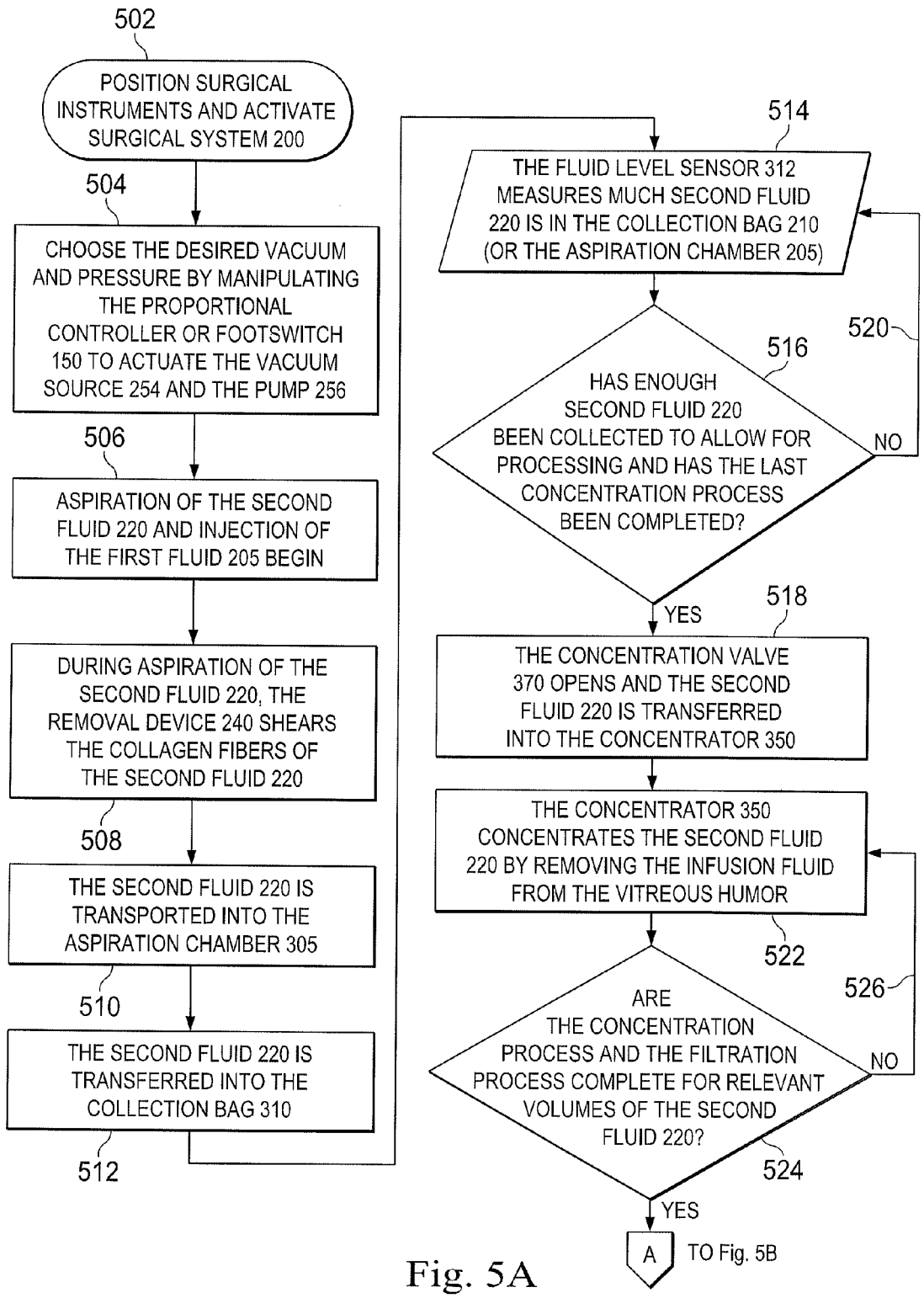
FIGS. 5a and 5b are flow charts illustrating a method of forming and using vitreous substitute using the microsurgical system shown in FIG. 2 according to one embodiment of the present disclosure.
Figure 5B:
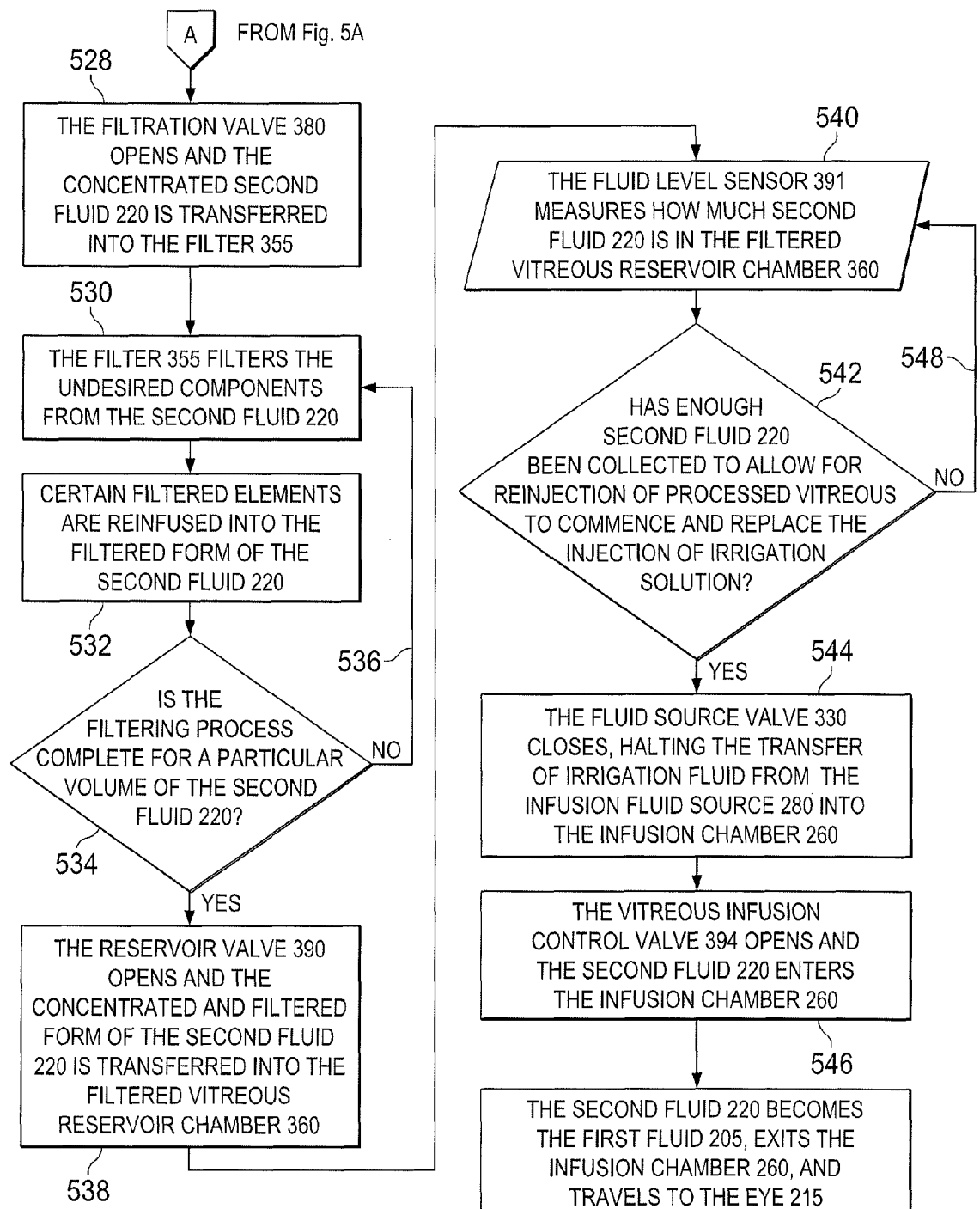

FIGS. 5a and 5b show a flow chart 500 representing an exemplary method of removing vitreous humor from an eye of a patient, preparing a vitreous substitute comprising a concentrated and filtered form of the vitreous humor, and re-injecting the vitreous substitute into the eye of the same patient during a single vitrectomy procedure. The method may be carried out by the surgical system 200 described above with reference to FIGS. 2-4. Although the method is depicted in flow chart form for the sake of clarity, it is important to note that many of the steps are performed in concert as opposed to in sequence.

The method begins at step 502, where the surgeon activates the surgical system 200 after accurately positioning the necessary surgical instruments for a conventional vitrectomy into the patient's eye. At step 504, the surgeon may choose the desired vacuum and pressure by manipulating the proportional controller or footswitch 150 to actuate the vacuum source 254 and the pump 256. Initially, the first fluid 205 is transferred from the infusion fluid source 280 into the infusion chamber 260 and injected into the eye. As discussed above, the flow rate of the first fluid 205 entering the posterior segment 210 is controlled by the surgical system 200 such that it substantially equally the flow rate of the second fluid 220 (i.e., the vitreous humor) exiting the posterior segment 210, resulting in a substantially constant volume of fluid in the eye 215 and the maintenance of an appropriate intraocular pressure.

At step 506, aspiration of the second fluid 220 and injection of the first fluid 205 begin. In some embodiments, aspiration of the second fluid 220 begins substantially simultaneously with injection of the first fluid 205. In one embodiment, the first fluid 205 initially comprises irrigation fluid (e.g., BSS) and the second fluid 220 comprises vitreous humor. Later in the procedure, the first fluid 205 may comprise a processed vitreous substitute, such as concentrated and filtered vitreous humor.

At step 508, as the surgeon uses the removal device 240 to aspirate the second fluid 220, the high cutting rate removal device (e.g., a vitreous cutter) shears the collagen fibers within the second fluid 220 (e.g., vitreous humor) into shorter segments, thereby disrupting the gel-like consistency of the vitreous humor.

At step 510, the second fluid 220 is transported via the aspiration conduit 310 into the aspiration chamber 305. In some embodiments, the second fluid 220 would only be allowed to enter the aspiration chamber if the control module allowed the aspiration valve 309 to open.

At step 512, the second fluid 220 is transferred from the aspiration chamber 305 into the collection bag 310. In the pictured embodiments, the collection bag 310 is coupled to the fluid level sensor 312, which determines the level of fluid within the collection bag 310. Some embodiments, as mentioned above, lack the collection bag and the fluid level sensor is configured to determine the level of fluid within the aspiration chamber. In either instance, at step 514, the fluid level sensor determines how much second fluid 220 is collected before being transferred to the processing system 300.

At step 516, the control module 400 of the system 200 queries whether enough second fluid 220 has been collected to allow for processing within the processing system 300. If the fluid level sensor measurement indicates that enough fluid 220 has been collected and the concentration process in the concentrator 350 is complete, at step 518, the control module 400 allows the concentration valve 370 to open and the second fluid 220 is transferred into the concentrator 350 via the concentration conduit 365. If, at step 520, the fluid level sensor measurement indicates that not enough fluid 220 has been collected or the last concentration process has not been completed, the control module 400 maintains the closed condition of the concentration valve 370 while more fluid 220 is aspirated from the eye, and the fluid level sensor continues to monitor the fluid levels within the collection bag 310.

At step 522, the concentrator 350 concentrates the second fluid 220 by separating and removing the infusion fluid (from the infusion fluid source 280) from the vitreous humor.

At step 524, the control module queries whether the concentration process is complete for the particular volume of the second fluid 220 that just underwent the concentration process and whether the filtration process is complete for the particular volume of the second fluid 220 that just underwent the filtration process. If, at step 526, the process is not complete or the filtration process for the current volume of second fluid 220 that just underwent the filtration is not complete, then the filtration valve 380 remains closed. If the process is complete, at step 528, then the control module allows the filtration valve 380 to open and the concentrated form of the second fluid 220 is transferred into the filter 355 via the filtration conduit 375.

At step 530, the filter 355 filters the undesired components from the concentrated form of the second fluid 220. As mentioned above, these undesired components include, by way of non-limiting example, red blood cells, white blood cells, cellular debris, foreign bodies, infectious material, and non-native particulates and precipitates (e.g., calcium). In some embodiments, the filtration and concentration processes are performed within a single device, as mentioned above. For example, in some embodiments, the filtration and concentration may be performed by a single centrifugal device. In some embodiments, the filter 355 and the concentrator 350 may be coupled to fluid level sensors substantially similar to the fluid level sensors 312, 391 described above.

At step 532, in some embodiments, certain filtered elements may be reinfused into the concentrated and filtered form of the second fluid 220. These filtered elements may include hyaluronan, ascorbate, and/or short collagen fragments.

At step 534, the control module queries whether the filtration process is complete for the particular volume of the second fluid 220 that just underwent the filtration process. If, at step 536, the process is not complete, then the filtration process continues within the filter 355 at step 530. If the process is complete, at step 538, then the control module allows the reservoir valve 390 to open and the concentrated and filtered form of the second fluid 220 is transferred into the filtered vitreous reservoir chamber 360 via the reservoir conduit 385.

At step 540, the fluid level sensor 391 measures how much second fluid 220 is in the filtered vitreous reservoir chamber 360. At step 542, the control module 400 of the system 200 queries whether enough concentrated and filtered second fluid 220 has been collected in the filtered vitreous reservoir chamber 360 to allow for reinjection of processed vitreous to commence and replace the injection of the first fluid irrigation solution. In the pictured embodiment, if the fluid level sensor measurement indicates that enough concentrated and filtered second fluid 220 has been collected, at step 544, the control module 400 closes the fluid source valve 330, thereby halting the flow of irrigation fluid from the infusion fluid source 280 into the infusion chamber 260, and, at step 546, allows the vitreous infusion control valve 394 to open, thereby allowing the concentrated and filtered second fluid 220 to enter the infusion chamber 260.

If the fluid level sensor measurement indicates that not enough concentrated and filtered second fluid 220 has been collected, at step 548, the vitreous infusion control valve 394 remains closed, injection into the eye of the first fluid 205 from the infusion fluid source 280 continues, and the fluid level sensor 391 continues to measure how much second fluid 220 is in the filtered vitreous reservoir chamber 360. Also, in some instances, if the surgical steps being performed necessitate the continued infusion of irrigation solution into the eye (e.g., such as during retinal repair), the system 200 is configured to keep the vitreous infusion control valve 394 closed and continue the flow of irrigation fluid into the eye even though the fluid level sensor measurement indicates that enough concentrated and filtered second fluid 220 has been collected. When the system 200 detects that the need for irrigation fluid has stopped, the system may allow the infusion of processed vitreous.

At step 550, the concentrated and filtered second fluid 220 becomes the first fluid 205, exits the infusion chamber 260, and travels to the eye 215. In particular, the first fluid (i.e., the vitreous substitute or processed vitreous) travels through the infusion port 322, the infusion conduit 320, the injection apparatus 340, the conduit 342, and the fluid infusion device 248 to enter the posterior segment 210 of the eye 215.

Instead of supplying a synthetic or non-autologous vitreous substitute, the vitreous substitutes disclosed herein comprise a processed (i.e., cut and filtered) form of the patient's own vitreous humor. Using a conventional vitrectomy surgical system and a processing system, the vitreous humor is removed from the patient's eye, processed, and re-injected into the patient's eye during a single vitrectomy procedure using a closed system in the operating room, which minimizes infection and contamination issues. The systems and methods disclosed herein allow for the preparation and use of a processed form of a patient's own vitreous humor, which retains the hyalocytes, hyaluronan, ascorbic acid (an antioxidant), and other factors that may be helpful in the prevention of ocular pathology related to vitrectomy, such as, by way of non-limiting example, nuclear sclerotic cataract. In addition, the systems and methods disclosed herein result in a processed form of a patient's own vitreous humor that lacks the undesired components within the native vitreous humor that may have been causing ocular problems for the patient. Additionally, the processed vitreous may be left permanently in the patient's eye without generating an immunological response. Moreover, the processed vitreous may provide clarity, transparency, and refractive index similar to the native vitreous humor, the ability to allow metabolite transfer, non-absorbable characteristics, hydrophilic composition, and the ability to be injected through a small-gauge needle.

In particular, the systems and methods disclosed herein are suitable for applications not involving retinal tamponade (unless the retinal tears have been repaired), including, by way of non-limiting example, vitreomacular surgery not requiring a gas bubble. The systems and methods disclosed herein utilizes conventional vitrectomy surgical tools and a processing system to re-inject processed vitreous that retains several helpful substances into the patient's eye, thereby allowing for autologous transplantation of a processed form of patient's own vitreous humor during a conventional vitrectomy procedure.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A system for removal of vitreous humor and other fluids from an eye and reinjection of filtered vitreous humor into the eye, the system comprising:

a hollow removal device including an element configured to cut the vitreous humor, the removal device configured to aspirate the vitreous humor from the eye;

a vacuum source configured to power the aspiration of the vitreous humor from the eye into the removal device;

an aspiration chamber, wherein the vacuum source is configured to power the aspiration of the vitreous humor from the eye into the aspiration chamber;

a first fluid level sensor coupled to the aspiration chamber, wherein the first fluid level sensor is configured to measure a level of fluid within the aspiration chamber;

a concentrator fluidly coupled to the aspiration chamber and configured to receive the fluid from the aspiration chamber when the first fluid level sensor detects a predetermined level of fluid in the aspiration chamber, wherein the concentrator is configured to create a concentrated form of the vitreous humor by separating the vitreous humor from the other fluids;

a filter fluidly coupled to the concentrator, wherein the filter is configured to receive the concentrated form of the vitreous humor and create a filtered form of the vitreous humor by separating the vitreous humor from undesired components in the vitreous humor;

a reservoir fluidly coupled to the filter and configured to receive the filtered form of the vitreous humor from the filter;

a second fluid level sensor coupled to the reservoir, wherein the second fluid level sensor is configured to measure a level of fluid within the reservoir;

an infusion device fluidly coupled to the reservoir and configured to return the filtered form of the vitreous humor into the eye when the second fluid level sensor measures a predetermined fluid level in the reservoir.

2. The system of claim 1, wherein the concentrator is configured to separate the vitreous humor from the other fluids by centrifugal force.

3. The system of claim 1, wherein the filter is configured to separate the vitreous humor from the other fluids by centrifugal force.

4. The system of claim 1, wherein the undesired components are selected from a group consisting of blood cells, cellular debris, foreign bodies, infectious material, and non-native precipitates and particulates.

5. The system of claim 1, wherein the filter comprises a mesh separator.

6. The system of claim 1, wherein the filter comprises a membrane separator.

7. The system of claim 6, wherein the membrane separator comprises a microfiber filter.

* * * * *